United States Patent [19]

Michaels

[11] Patent Number: 6,096,865

[45] Date of Patent: Aug. 1, 2000

[54] MUTANTS OF THE GREEN FLUORESCENT PROTEIN HAVING IMPROVED FLUORESCENT PROPERTIES AT 37°

[75] Inventor: Mark Michaels, Encino, Calif.

[73] Assignee: Amgen Inc., Thousand Oaks, Calif.

[21] Appl. No.: 08/643,704

[22] Filed: May 6, 1996

[51] Int. Cl.[7] .................. C07K 14/435; C12N 15/11; C12N 5/10

[52] U.S. Cl. .................. 530/350; 536/23.5; 536/23.1; 435/69.1; 435/320.1; 435/325; 435/252.3; 435/254.11

[58] Field of Search .................. 436/501; 530/350; 435/325, 252.3, 254.11, 7.2, 69.1, 40.5, 320.1; 536/23.1, 23.5

[56] References Cited

U.S. PATENT DOCUMENTS

| | | | |
|---|---|---|---|
| 4,861,709 | 8/1989 | Ulitzur et al. | 435/6 |
| 5,360,728 | 11/1994 | Prasher | 435/189 |
| 5,804,387 | 9/1998 | Cormack et al. | |

FOREIGN PATENT DOCUMENTS

95/07463  3/1995  WIPO .

OTHER PUBLICATIONS

Schulz et al., Principles of Protein Structure, Springer–Verlag: New York, pp. 14–16, 1979.

Titus, Ed., Promega Protocols and Applications Guide, Promega: USA, pp. 299 and 310, 1991.

Prasher et al., Primary structure of the *Aequorea victorea* green–fluorescent protein, Gene, 111(2): 229–233, Feb. 1992.

Heim et al., Enginerring the green fluorescent protien for improved brightness, longer wavelengths and fluorescence resonance energy transfer, Curr. Biol., 6(2): 178–182, Feb. 1996.

Barthmaier, Peter and Fyrberg, Eric, "Monitoring Development and Pathology of Drosophila Indirect Flight Muscles Using Green Fluorescent Protein", *Developmental Biology,* 169: 770–774 (1995).

Chalfie, et al., "Green Fluorescent Protein as a Marker for Gene Expression", *Science,* 263: 802–805 (1994).

Cormack, et al., "FACS–Optimized Mutants of the Green Fluorescent Protein (GFP)", *Gene,* 173: 33–38 (1996).

Crameri, et al., "Improved Green Fluorescent Protenin By Molecular Evolution Using DNA Shuffling", *Nature Biotechnology,* 14: 315–319 (1996).

Delagrave, et al., "Red–Shifted Excitation Mutants of the Green Fluorescent Protein", *Bio/Technology,* 13: 151–154 (1995).

Heim, et al., "Improved Green Fluorescence", *Nature,* 373: 663–664 (1995).

Heim, et al., "Wavelength Mutations and Posttranslational Autoxidation of Green Fluorescent Protein", *Proc. Natl. Acad. Sci. USA,* 91: 12501–12504 (1994).

*Primary Examiner*—Lorraine Spector
*Assistant Examiner*—Claire M. Kaufman
*Attorney, Agent, or Firm*—Craig A. Crandall; Ron K. Levy; Steven M. Odre

[57] ABSTRACT

The present invention relates to mutants of the green fluorescent protein having improved fluorescent properties at 37° C. The mutants provide for improved methods of monitoring gene expression, e.g., for use as cell markers or protein expression indicators in prokaryotic and, especially, eucaryotic systems where the standard physiological temperature is 37° C.

6 Claims, No Drawings

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 60 base pairs
      (B) TYPE: nucleic acid
      (C) STRANDEDNESS: unknown
      (D) TOPOLOGY: unknown (ii) MOLECULE TYPE: cDNA (xi) SEQUENCE DESCRIPTION: SEQ ID NO:1:

GAACTTTTCA CTGGAGTGGT ACCAATACTA GTTGAATTAG ATGGTGATGT TAATGGGCAC    60

(2) INFORMATION FOR SEQ ID NO:2:

(i) SEQUENCE CHARACTERISTICS:
      (A) LENGTH: 60 base pairs
      (B) TYPE: nucleic acid
      (C) STRANDEDNESS: unknown
      (D) TOPOLOGY: unknown (ii) MOLECULE TYPE: cDNA (xi) SEQUENCE DESCRIPTION: SEQ ID NO:2:

AAATTTTCTG TCAGTGGAGA GGGTGAAGGT GATGCAACAT ACGGAAAACT TACCCTTAAA        60

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:3:

TTTATTTGCA CTACTGGAAA ACTACCTGTT CCATGGCCAA CACTTGTCAC TACTTTCTCT        60

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:4:

TATGGTGTTC AATGCTTTTC AAGATACCCA GATCACATGA AACAGCATGA CTTTTTCAAG        60

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:5:

AGTGCCATGC CCGAAGGTTA TGTACAGGAA AGAACTATAT TTTTCAAAGA TGACGGGAAC        60

(2) INFORMATION FOR SEQ ID NO:6:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:6:

TACAAGACAC GTGCTGAAGT CAAGTTTGAA GGTGATACCC TTGTTAATAG AATCGAGTTA        60

(2) INFORMATION FOR SEQ ID NO:7:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:7:

AAAGGTATTG ATTTTAAAGA AGATGGAAAC ATTCTTGGAC ACAAATTGGA ATACAACTAT        60

(2) INFORMATION FOR SEQ ID NO:8:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:8:

AACTCACACA ATGTATACAT CATGGCAGAC AAACAAAAGA ATGGAATCAA AGTTAACTTC    60

(2) INFORMATION FOR SEQ ID NO:9:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:9:

AAAATTAGAC ACAACATTGA AGATGGAAGC GTTCAACTAG CAGACCATTA TCAACAAAAT    60

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:10:

ACTCCAATTG GCGATGGCCC AGTACTTTTA CCAGACAACC ATTACCTGTC CACACAATCT    60

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:11:

GCCCTTTCGA AAGATCCCAA CGAAAAGAGA GACCACATGG TCCTTCTTGA ATTCGTAACA    60

(2) INFORMATION FOR SEQ ID NO:12:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:12:

GCTGCAGGGA TTACACATGG CATGGATGAG CTCTACAAAT AAGCTTGGAT CCGCTTGGGC    60

(2) INFORMATION FOR SEQ ID NO:13:

(i) SEQUENCE CHARACTERISTICS:
        (A) LENGTH: 60 base pairs
        (B) TYPE: nucleic acid (C) STRANDEDNESS: unknown
            (D) TOPOLOGY: unknown (ii) MOLECULE TYPE: cDNA (xi) SEQUENCE DESCRIPTION: SEQ ID NO:13:

CTCATCCATG CCATGTGTAA TCCCTGCAGC TGTTACGAAT TCAAGAAGGA CCATGTGGTC     60

(2) INFORMATION FOR SEQ ID NO:14:

(i) SEQUENCE CHARACTERISTICS:
            (A) LENGTH: 60 base pairs
            (B) TYPE: nucleic acid
            (C) STRANDEDNESS: unknown
            (D) TOPOLOGY: unknown (ii) MOLECULE TYPE: cDNA (xi) SEQUENCE DESCRIPTION: SEQ ID NO:14:

TCTCTTTTCG TTGGGATCTT TCGAAAGGGC AGATTGTGTG GACAGGTAAT GGTTGTCTGG     60

(2) INFORMATION FOR SEQ ID NO:15:

(i) SEQUENCE CHARACTERISTICS:
            (A) LENGTH: 60 base pairs
            (B) TYPE: nucleic acid
            (C) STRANDEDNESS: unknown
            (D) TOPOLOGY: unknown (ii) MOLECULE TYPE: cDNA (xi) SEQUENCE DESCRIPTION: SEQ ID NO:15:

TAAAAGTACT GGGCCATCGC CAATTGGAGT ATTTTGTTGA TAATGGTCTG CTAGTTGAAC     60

(2) INFORMATION FOR SEQ ID NO:16:

(i) SEQUENCE CHARACTERISTICS:
            (A) LENGTH: 60 base pairs
            (B) TYPE: nucleic acid
            (C) STRANDEDNESS: unknown
            (D) TOPOLOGY: unknown (ii) MOLECULE TYPE: cDNA (xi) SEQUENCE DESCRIPTION: SEQ ID NO:16:

GCTTCCATCT TCAATGTTGT GTCTAATTTT GAAGTTAACT TTGATTCCAT TCTTTTGTTT     60

(2) INFORMATION FOR SEQ ID NO:17:

(i) SEQUENCE CHARACTERISTICS:
            (A) LENGTH: 60 base pairs
            (B) TYPE: nucleic acid
            (C) STRANDEDNESS: unknown
            (D) TOPOLOGY: unknown (ii) MOLECULE TYPE: cDNA (xi) SEQUENCE DESCRIPTION: SEQ ID NO:17:

GTCTGCCATG ATGTATACAT TGTGTGAGTT ATAGTTGTAT TCCAATTTGT GTCCAAGAAT     60

(2) INFORMATION FOR SEQ ID NO:18:

(i) SEQUENCE CHARACTERISTICS:
            (A) LENGTH: 60 base pairs
            (B) TYPE: nucleic acid
            (C) STRANDEDNESS: unknown
            (D) TOPOLOGY: unknown (ii) MOLECULE TYPE: cDNA (xi) SEQUENCE DESCRIPTION: SEQ ID NO:18:

GTTTCCATCT TCTTTAAAAT CAATACCTTT TAACTCGATT CTATTAACAA GGGTATCACC    60

(2) INFORMATION FOR SEQ ID NO:19:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:19:

TTCAAACTTG ACTTCAGCAC GTGTCTTGTA GTTCCCGTCA TCTTTGAAAA ATATAGTTCT    60

(2) INFORMATION FOR SEQ ID NO:20:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:20:

TTCCTGTACA TAACCTTCGG GCATGGCACT CTTGAAAAAG TCATGCTGTT TCATGTGATC    60

(2) INFORMATION FOR SEQ ID NO:21:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:21:

TGGGTATCTT GAAAAGCATT GAACACCATA AGAGAAAGTA GTGACAAGTG TTGGCCATGG    60

(2) INFORMATION FOR SEQ ID NO:22:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:22:

AACAGGTAGT TTTCCAGTAG TGCAAATAAA TTTAAGGGTA AGTTTTCCGT ATGTTGCATC    60

(2) INFORMATION FOR SEQ ID NO:23:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:23:

ACCTTCACCC TCTCCACTGA CAGAAAATTT GTGCCCATTA ACATCACCAT CTAATTCAAC    60

(2) INFORMATION FOR SEQ ID NO:24:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:24:

TAGTATTGGT ACCACTCCAG TGAAAAGTTC TTCTCCTTTA CTCATATGTT ATTCCTCCTT      60

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:25:

CTAGAATCAA ATCGATGACG T      21

(2) INFORMATION FOR SEQ ID NO:26:

(i) SEQUENCE CHARACTERISTICS:
        (A) LENGTH: 47 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:26:

CATCGATTTG ATTCTAGAAG GAGGAATAAC ATATGAGTAA AGGAGAA      47

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:27:

GCCCAAGCGG ATCCAAGCTT ATTTGTAGAG      30

(2) INFORMATION FOR SEQ ID NO:28:

(i) SEQUENCE CHARACTERISTICS:
        (A) LENGTH: 53 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:28:

CCAGGACGCT CCAGAAGGAG GAATAACATA TGAGTAAAGG AGAAGAACTT TTC      53

(2) INFORMATION FOR SEQ ID NO:29:

(i) SEQUENCE CHARACTERISTICS:
    (A) LENGTH: 24 base pairs
    (B) TYPE: nucleic acid
    (C) STRANDEDNESS: unknown
    (D) TOPOLOGY: unknown (ii) MOLECULE TYPE: cDNA (xi) SEQUENCE DESCRIPTION: SEQ ID NO:29:

ACCCAGTAAG GCAGCGGTAT CATC                                              24

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:30:

GGTCATTACT GGACCGGATC                                                   20

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:31:

ACTGACAGAA AATTTGTGCC CATTAACAT                                         29

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:32:

TCTGTCAGTG GAGAGGGTGA AGGTGA                                            26

(2) INFORMATION FOR SEQ ID NO:33:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:33:

TGACTTGTAG TTCCCGTCAT CTTTGTAAAA TATAGTTCTT TC                          42

(2) INFORMATION FOR SEQ ID NO:34:

(i) SEQUENCE CHARACTERISTICS:
        (A) LENGTH: 42 base pairs
        (B) TYPE: nucleic acid
        (C) STRANDEDNESS: unknown (D) TOPOLOGY: unknown (ii) MOLECULE TYPE: cDNA (xi) SEQUENCE DESCRIPTION: SEQ ID NO:34:

TTTACAAAGA TGACGGGAAC TACAAGTCAC GTGCTGAAGT CA                              42

(2) INFORMATION FOR SEQ ID NO:35:

(i) SEQUENCE CHARACTERISTICS:
           (A) LENGTH: 22 base pairs
           (B) TYPE: nucleic acid
           (C) STRANDEDNESS: unknown
           (D) TOPOLOGY: unknown (ii) MOLECULE TYPE: cDNA (xi) SEQUENCE DESCRIPTION: SEQ ID NO:35:

TATTCCATTT TGTGTCCAAG AA                                                   22

(2) INFORMATION FOR SEQ ID NO:36:

(i) SEQUENCE CHARACTERISTICS:
           (A) LENGTH: 26 base pairs
           (B) TYPE: nucleic acid
           (C) STRANDEDNESS: unknown
           (D) TOPOLOGY: unknown (ii) MOLECULE TYPE: cDNA (xi) SEQUENCE DESCRIPTION: SEQ ID NO:36:

GGACACAAAA TGGAATACAA CTATAA                                               26

(2) INFORMATION FOR SEQ ID NO:37:

(i) SEQUENCE CHARACTERISTICS:
           (A) LENGTH: 39 base pairs
           (B) TYPE: nucleic acid
           (C) STRANDEDNESS: unknown
           (D) TOPOLOGY: unknown (ii) MOLECULE TYPE: cDNA (xi) SEQUENCE DESCRIPTION: SEQ ID NO:37:

GCTGTTACGA ATTCAAGAAG GATCATGTGG TCTCTCTTT                                 39

(2) INFORMATION FOR SEQ ID NO:38:

(i) SEQUENCE CHARACTERISTICS:
           (A) LENGTH: 26 base pairs
           (B) TYPE: nucleic acid
           (C) STRANDEDNESS: unknown
           (D) TOPOLOGY: unknown (ii) MOLECULE TYPE: cDNA (xi) SEQUENCE DESCRIPTION: SEQ ID NO:38:

AACACCATGA GAGAGAGTAG TGACAA                                               26

(2) INFORMATION FOR SEQ ID NO:39:

(i) SEQUENCE CHARACTERISTICS:
           (A) LENGTH: 29 base pairs
           (B) TYPE: nucleic acid
           (C) STRANDEDNESS: unknown
           (D) TOPOLOGY: unknown (ii) MOLECULE TYPE: cDNA (xi) SEQUENCE DESCRIPTION: SEQ ID NO:39:

TCTCTCATGG TGTTCAATGC TTTTCAAGA                                                  29

(2) INFORMATION FOR SEQ ID NO:40:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:40:

AAGGGTATCA CCTTCAAACT TGACTT                                                     26

(2) INFORMATION FOR SEQ ID NO:41:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:41:

GACCGCATCG ATTTGATTCT AGAAGGAGGA AT                                              32

(2) INFORMATION FOR SEQ ID NO:42:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:42:

TATTGGTACC ACTCCAGTGA AAAGTTCTCC TTTACTCATA GT                                   42

(2) INFORMATION FOR SEQ ID NO:43:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:43:

ATCGAGTGGT GTATTTATCA ATATTG                                                     26

(2) INFORMATION FOR SEQ ID NO:44:

(i) SEQUENCE CHARACTERISTICS:
        (A) LENGTH: 714 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION: 1..714

(xi) SEQUENCE DESCRIPTION: SEQ ID NO:44:

```
ATG AGT AAA GGA GAA GAA CTT TTC ACT GGA GTG GTA CCA ATA CTA GTT      48
Met Ser Lys Gly Glu Glu Leu Phe Thr Gly Val Val Pro Ile Leu Val
  1               5                  10                  15

GAA TTA GAT GGT GAT GTT AAT GGG CAC AAA TTT TCT GTC AGT GGA GAG      96
Glu Leu Asp Gly Asp Val Asn Gly His Lys Phe Ser Val Ser Gly Glu
                 20                  25                  30

GGT GAA GGT GAT GCA ACA TAC GGA AAA CTT ACC CTT AAA TTT ATT TGC     144
Gly Glu Gly Asp Ala Thr Tyr Gly Lys Leu Thr Leu Lys Phe Ile Cys
             35                  40                  45

ACT ACT GGA AAA CTA CCT GTT CCA TGG CCA ACA CTT GTC ACT ACT CTC     192
Thr Thr Gly Lys Leu Pro Val Pro Trp Pro Thr Leu Val Thr Thr Leu
         50                  55                  60

TCT TAT GGT GTT CAA TGC TTT TCA AGA TAC CCA GAT CAC ATG AAA CAG     240
Ser Tyr Gly Val Gln Cys Phe Ser Arg Tyr Pro Asp His Met Lys Gln
 65                  70                  75                  80

CAT GAC TTT TTC AAG AGT GCC ATG CCC GAA GGT TAT GTA CAG GAA AGA     288
His Asp Phe Phe Lys Ser Ala Met Pro Glu Gly Tyr Val Gln Glu Arg
                 85                  90                  95

ACT ATA TTT TAC AAA GAT GAC GGG AAC TAC AAG TCA CGT GCT GAA GTC     336
Thr Ile Phe Tyr Lys Asp Asp Gly Asn Tyr Lys Ser Arg Ala Glu Val
            100                 105                 110

AAG TTT GAA GGT GAT ACC CTT GTT AAT AGA ATC GAG TTA AAA GGT ATT     384
Lys Phe Glu Gly Asp Thr Leu Val Asn Arg Ile Glu Leu Lys Gly Ile
        115                 120                 125

GAT TTT AAA GAA GAT GGA AAC ATT CTT GGA CAC AAA ATG GAA TAC AAC     432
Asp Phe Lys Glu Asp Gly Asn Ile Leu Gly His Lys Met Glu Tyr Asn
    130                 135                 140

TAT AAC TCA CAC AAT GTA TAC ATC ATG GCA GAC AAA CAA AAG AAT GGA     480
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT     528
Ile Lys Val Asn Phe Lys Ile Arg His Asn Ile Glu Asp Gly Ser Val
                165                 170                 175

CAA CTA GCA GAC CAT TAT CAA CAA AAT ACT CCA ATT GGC GAT GGC CCA     576
Gln Leu Ala Asp His Tyr Gln Gln Asn Thr Pro Ile Gly Asp Gly Pro
            180                 185                 190

GTA CTT TTA CCA GAC AAC CAT TAC CTG TCC ACA CAA TCT GCC CTT TCG     624
Val Leu Leu Pro Asp Asn His Tyr Leu Ser Thr Gln Ser Ala Leu Ser
        195                 200                 205

AAA GAT CCC AAC GAA AAG AGA GAC CAC ATG ATC CTT CTT GAA TTC GTA     672
Lys Asp Pro Asn Glu Lys Arg Asp His Met Ile Leu Leu Glu Phe Val
    210                 215                 220

ACA GCT GCA GGG ATT ACA CAT GGC ATG GAT GAG CTC TAC AAA             714
Thr Ala Ala Gly Ile Thr His Gly Met Asp Glu Leu Tyr Lys
225                 230                 235
```

(2) INFORMATION FOR SEQ ID NO:45:

(i) SEQUENCE CHARACTERISTICS:
        (A) LENGTH: 540 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:45:

```
ACATAAATAC CACTGGCGGT GATACTGAGC ACATCGATTT GATTCTAGAA GGAGGAATAA      60

CATATGTACG ACTACATGGA AGGTGGTGAC ATCCGCGTAC GTCGTCTGTT CTGCCGTACC     120
```

```
CAGTGGTACC TGCGTATCGA CAAACGCGGC AAAGTCAAGG GCACCCAAGA GATGAAAAAC        180

AACTACAATA TTATGGAAAT CCGTACTGTT GCTGTTGGTA TCGTTGCAAT CAAAGGTGTT        240

GAATCTGAAT TCTACCTGGC AATGAACAAA GAAGGTAAAC TGTACGCAAA AAAAGAATGC        300

AACGAAGACT GCAACTTCAA AGAACTGATC CTGGAAAACC ACTACAACAC CTACGCATCT        360

GCTAAATGGA CCCACAACGG TGGTGAAATG TTCGTTGCTC TGAACCAGAA AGGTATCCCG        420

GTTCGTGGTA AAAAAACCAA AAAAGAACAG AAAACCGCTC ACTTCCTGCC GATGGCAATC        480

ACTTAATAGG ATCCGCGGAT AAATAAGTAA CGATCCGGTC CAGTAATGAC CTCAGAACTC        540

(2) INFORMATION FOR SEQ ID NO:46:

(i) SEQUENCE CHARACTERISTICS:
         (A) LENGTH: 900 base pairs
         (B) TYPE: nucleic acid
         (C) STRANDEDNESS: unknown
         (D) TOPOLOGY: unknown (ii) MOLECULE TYPE: cDNA (xi) SEQUENCE DESCRIPTION: SEQ ID NO:46:

ATTCATGTTG ATGATTTATT ATATATCGAG TGGTGTATTT ATCAATATTG TTTGCTCCGT         60

TATCGTTATT AACACCAGCC TATCGATTTG ATTCTAGAAG GAGGAATAAC ATATGAGTAA        120

AGGAGAAGAA CTTTTCACTG GAGTGGTACC AATACTAGTT GAATTAGATG GTGATGTTAA        180

TGGGCACAAA TTTTCTATCA GTGGAGAGGG TGAAGGTGAT GCAACATACG GAAAACTTAC        240

CCTTAAATTT ATTTGCACTA CTGGAAAACT ACCTGTTCCA TGGCCAACAC TTGTCACTAC        300

TCTCTCTTAT GGTGTTCAAT GCTTTTCAAG ATACCCAGAT CACATGAAAC AGCATGACTT        360

TTTCAAGAGT GCCATGCCCG AAGGTTATGT ACAGGAAAGA ACTATATTTT ACAAAGATGA        420

CGGGAACTAC AAGTCACGTG CTGAAGTCAA GTTTGAAGGT GATACCCTTG TTAATAGAAT        480

CGAGTTAAAA GGTATTGATT TTAAAGAAGA TGGAAACATT CTTGGACACA AAATGGAATA        540

CAACTATAAC TCACACAATG TATACATCAT GGCAGACAAA CAAAAGAATG GAATCAAAGT        600

TAACTTCAAA ATTAGACACA ACATTGAAGA TGGAAGCGTT CAACTAGCAG ACCATTATCA        660

ACAAAATACT CCAATTGGCG ATGGCCCAGT ACTTTTACCA GACAACCATT ACCTGTCCAC        720

ACAATCTGCC CTTTCGAAAG ATCCCAACGA AAAGAGAGAC CACATGATCC TTCTTGAATT        780

CGTAACAGCT GCAGGGATTA CACATGGCAT GGATGAGCTC TACAAATAAG CTTACTCGAG        840

GATCCGCGGA TAAATAAGTA ACGATCCGGT CCAGTAATGA CCTCAGAACT CCATCTGGAT        900

(2) INFORMATION FOR SEQ ID NO:47:

(i) SEQUENCE CHARACTERISTICS:
         (A) LENGTH: 816 base pairs
         (B) TYPE: nucleic acid
         (C) STRANDEDNESS: unknown
         (D) TOPOLOGY: unknown (ii) MOLECULE TYPE: cDNA (ix) FEATURE:
         (A) NAME/KEY: CDS
         (B) LOCATION: 1..816

(xi) SEQUENCE DESCRIPTION: SEQ ID NO:47:

ATG AGT AAA GGA GAA GAA CTT TTC ACT GGA GTG GTA CCA ATA CTA GTT         48
Met Ser Lys Gly Glu Glu Leu Phe Thr Gly Val Val Pro Ile Leu Val
 1               5                  10                  15

GAA TTA GAT GGT GAT GTT AAT GGG CAC AAA TTT TCT GTC AGT GGA GAG         96
```

```
        Glu Leu Asp Gly Asp Val Asn Gly His Lys Phe Ser Val Ser Gly Glu
                     20                  25                  30

GGT GAA GGT GAT GCA ACA TAC GGA AAA CTT ACC CTT AAA TTT ATT TGC       144
Gly Glu Gly Asp Ala Thr Tyr Gly Lys Leu Thr Leu Lys Phe Ile Cys
         35                  40                  45

ACT ACT GGA AAA CTA CCT GTT CCA TGG CCA ACA CTT GTC ACT ACT CTC       192
Thr Thr Gly Lys Leu Pro Val Pro Trp Pro Thr Leu Val Thr Thr Leu
 50                  55                  60

TCT TAT GGT GTT CAA TGC TTT TCA AGA TAC CCA GAT CAC ATG AAA CAG       240
Ser Tyr Gly Val Gln Cys Phe Ser Arg Tyr Pro Asp His Met Lys Gln
 65                  70                  75                  80

CAT GAC TTT TTC AAG AGT GCC ATG CCC GAA GGT TAT GTA CAG GAA AGA       288
His Asp Phe Phe Lys Ser Ala Met Pro Glu Gly Tyr Val Gln Glu Arg
             85                  90                  95

ACT ATA TTT TAC AAA GAT GAC GGG AAC TAC AAG TCA CGT GCT GAA GTC       336
Thr Ile Phe Tyr Lys Asp Asp Gly Asn Tyr Lys Ser Arg Ala Glu Val
            100                 105                 110

AAG TTT GAA GGT GAT ACC CTT GTT AAT AGA ATC GAG TTA AAA GGT ATT       384
Lys Phe Glu Gly Asp Thr Leu Val Asn Arg Ile Glu Leu Lys Gly Ile
        115                 120                 125

GAT TTT AAA GAA GAT GGA AAC ATT CTT GGA CAC AAA ATG GAA TAC AAC       432
Asp Phe Lys Glu Asp Gly Asn Ile Leu Gly His Lys Met Glu Tyr Asn
130                 135                 140

TAT AAC TCA CAC AAT GTA TAC ATC ATG GCA GAC AAA CAA AAG AAT GGA       480
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT       528
Ile Lys Val Asn Phe Lys Ile Arg His Asn Ile Glu Asp Gly Ser Val
                165                 170                 175

CAA CTA GCA GAC CAT TAT CAA CAA AAT ACT CCA ATT GGC GAT GGC CCA       576
Gln Leu Ala Asp His Tyr Gln Gln Asn Thr Pro Ile Gly Asp Gly Pro
            180                 185                 190

GTA CTT TTA CCA GAC AAC CAT TAC CTG TCC ACA CAA TCT GCC CTT TCG       624
Val Leu Leu Pro Asp Asn His Tyr Leu Ser Thr Gln Ser Ala Leu Ser
            195                 200                 205

AAA GAT CCC AAC GAA AAG AGA GAC CAC ATG ATC CTT CTT GAA TTC GTA       672
Lys Asp Pro Asn Glu Lys Arg Asp His Met Ile Leu Leu Glu Phe Val
        210                 215                 220

ACA GCT GCA GGG ATT ACA CAT GGC ATG GAT GAG CTC TAC AAA CAC CAC       720
Thr Ala Ala Gly Ile Thr His Gly Met Asp Glu Leu Tyr Lys His His
225                 230                 235                 240

CAC CAC CAC CAT GAA CAG AAA CTG ATC TCC GAA GAA GAC CTG AAC AAC       768
His His His His Glu Gln Lys Leu Ile Ser Glu Glu Asp Leu Asn Asn
                245                 250                 255

AAC AAC AAC AAC AAC AAC CGT CCA CCA GGT TTC TCC CCG TTC CGT           816
Asn Asn Asn Asn Asn Asn Arg Pro Pro Gly Phe Ser Pro Phe Arg
            260                 265                 270

(2) INFORMATION FOR SEQ ID NO:48:

(i) SEQUENCE CHARACTERISTICS:
        (A) LENGTH: 1236 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION: 1..1236

(xi) SEQUENCE DESCRIPTION: SEQ ID NO:48:
```

```
ATG AGT AAA GGA GAA GAA CTT TTC ACT GGA GTG GTA CCA ATA CTA GTT      48
Met Ser Lys Gly Glu Glu Leu Phe Thr Gly Val Val Pro Ile Leu Val
 1               5                  10                  15

GAA TTA GAT GGT GAT GTT AAT GGG CAC AAA TTT TCT GTC AGT GGA GAG      96
Glu Leu Asp Gly Asp Val Asn Gly His Lys Phe Ser Val Ser Gly Glu
             20                  25                  30

GGT GAA GGT GAT GCA ACA TAC GGA AAA CTT ACC CTT AAA TTT ATT TGC     144
Gly Glu Gly Asp Ala Thr Tyr Gly Lys Leu Thr Leu Lys Phe Ile Cys
         35                  40                  45

ACT ACT GGA AAA CTA CCT GTT CCA TGG CCA ACA CTT GTC ACT ACT CTC     192
Thr Thr Gly Lys Leu Pro Val Pro Trp Pro Thr Leu Val Thr Thr Leu
     50                  55                  60

TCT TAT GGT GTT CAA TGC TTT TCA AGA TAC CCA GAT CAC ATG AAA CAG     240
Ser Tyr Gly Val Gln Cys Phe Ser Arg Tyr Pro Asp His Met Lys Gln
 65                  70                  75                  80

CAT GAC TTT TTC AAG AGT GCC ATG CCC GAA GGT TAT GTA CAG GAA AGA     288
His Asp Phe Phe Lys Ser Ala Met Pro Glu Gly Tyr Val Gln Glu Arg
                 85                  90                  95

ACT ATA TTT TAC AAA GAT GAC GGG AAC TAC AAG TCA CGT GCT GAA GTC     336
Thr Ile Phe Tyr Lys Asp Asp Gly Asn Tyr Lys Ser Arg Ala Glu Val
             100                 105                 110

AAG TTT GAA GGT GAT ACC CTT GTT AAT AGA ATC GAG TTA AAA GGT ATT     384
Lys Phe Glu Gly Asp Thr Leu Val Asn Arg Ile Glu Leu Lys Gly Ile
         115                 120                 125

GAT TTT AAA GAA GAT GGA AAC ATT CTT GGA CAC AAA ATG GAA TAC AAC     432
Asp Phe Lys Glu Asp Gly Asn Ile Leu Gly His Lys Met Glu Tyr Asn
     130                 135                 140

TAT AAC TCA CAC AAT GTA TAC ATC ATG GCA GAC AAA CAA AAG AAT GGA     480
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT     528
Ile Lys Val Asn Phe Lys Ile Arg His Asn Ile Glu Asp Gly Ser Val
                 165                 170                 175

CAA CTA GCA GAC CAT TAT CAA CAA AAT ACT CCA ATT GGC GAT GGC CCA     576
Gln Leu Ala Asp His Tyr Gln Gln Asn Thr Pro Ile Gly Asp Gly Pro
             180                 185                 190

GTA CTT TTA CCA GAC AAC CAT TAC CTG TCC ACA CAA TCT GCC CTT TCG     624
Val Leu Leu Pro Asp Asn His Tyr Leu Ser Thr Gln Ser Ala Leu Ser
         195                 200                 205

AAA GAT CCC AAC GAA AAG AGA GAC CAC ATG ATC CTT CTT GAA TTC GTA     672
Lys Asp Pro Asn Glu Lys Arg Asp His Met Ile Leu Leu Glu Phe Val
     210                 215                 220

ACA GCT GCA GGG ATT ACA CAT GGC ATG GAT GAG CTC TAC AAA CAC CAC     720
Thr Ala Ala Gly Ile Thr His Gly Met Asp Glu Leu Tyr Lys His His
225                 230                 235                 240

CAC CAC CAC CAT GAA CAG AAA CTG ATC TCC GAA GAA GAC CTG AAC AAC     768
His His His His Glu Gln Lys Leu Ile Ser Glu Glu Asp Leu Asn Asn
                 245                 250                 255

AAC AAC AAC AAC AAC AAC CGT CCA CCA GGT TTC TCC CCG TTC CGT         816
Asn Asn Asn Asn Asn Asn Arg Pro Pro Gly Phe Ser Pro Phe Arg
             260                 265                 270

TCC TAC GAC TAC ATG GAA GGT GGT GAA ATC CGC GTA CGT CGT CTG TTC     864
Ser Tyr Asp Tyr Met Glu Gly Gly Glu Ile Arg Val Arg Arg Leu Phe
         275                 280                 285

TGC CGT ACC CAG TGG TAC CTG CGT ATC GAC AAA CGC GGC AAA GTC AAG     912
Cys Arg Thr Gln Trp Tyr Leu Arg Ile Asp Lys Arg Gly Lys Val Lys
     290                 295                 300

GGC ACC CAA GAG ATG AAA AAC AAC TAC AAT ATT ATG GAA ATC CGT ACT     960
Gly Thr Gln Glu Met Lys Asn Asn Tyr Asn Ile Met Glu Ile Arg Thr
```

```
                305                  310                 315                 320
GTT GCT GTT GGT ATC GTT GCA ATC AAA GGT GTT GAA TCT GAA TTC TAC       1008
Val Ala Val Gly Ile Val Ala Ile Lys Gly Val Glu Ser Glu Phe Tyr
                    325                 330                 335

CTG GCA ATG AAC AAA GAA GGT AAA CTG TAC GCA AAA AAA GAA TGC AAC       1056
Leu Ala Met Asn Lys Glu Gly Lys Leu Tyr Ala Lys Lys Glu Cys Asn
                340                 345                 350

GAA GAC TGC AAC TTC AAA GAA CTG ATC CTG GAA AAC CAC TAC AAC ACC       1104
Glu Asp Cys Asn Phe Lys Glu Leu Ile Leu Glu Asn His Tyr Asn Thr
            355                 360                 365

TAC GCA TCT GCT AAA TGG ACC CAC AAC GGT GGT GAA ATG TTC GTT GCT       1152
Tyr Ala Ser Ala Lys Trp Thr His Asn Gly Gly Glu Met Phe Val Ala
        370                 375                 380

CTG AAC CAG AAA GGT ATC CCG GTT CGT GGT AAA AAA ACC AAA AAA GAA       1200
Leu Asn Gln Lys Gly Ile Pro Val Arg Gly Lys Lys Thr Lys Lys Glu
385                 390                 395                 400

CAG AAA ACC GCT CAC TTC CTG CCG ATG GCA ATC ACT                       1236
Gln Lys Thr Ala His Phe Leu Pro Met Ala Ile Thr
                405                 410
```

(2) INFORMATION FOR SEQ ID NO:49:

(i) SEQUENCE CHARACTERISTICS:
        (A) LENGTH: 238 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:49:

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Ser Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
```

-continued

```
            210                 215                 220
Thr Ala Ala Gly Ile Thr His Gly Met Asp Glu Leu Tyr Lys
225                 230                 235
```

MUTANTS OF THE GREEN FLUORESCENT PROTEIN HAVING IMPROVED FLUORESCENT PROPERTIES AT 37°

BACKGROUND OF THE INVENTION

The green fluorescent protein (GFP) is a 238 amino acid molecule which is the ultimate source of fluorescent light emission in the jellyfish *Aequorea victoria.* The GFP excitation spectrum shows an absorption band (blue light) maximally at 395 nm with a minor peak at 470 nm, and an emission peak (green light) at 509 nm. The longer-wavelength excitation peak has greater photostability then the shorter peak, but is relatively low in amplitude; Chalfie et al., Science, 263:802–805 (1994). The GFP absorption bands and emission peak arise from an internal p-hydroxybenzylidene-imidazolidinone chromophore, which is generated by cyclization and oxidation of a Ser-Tyr-Gly sequence at residues 65–67; Cody et al. *Biochemistry* 32:1212–1218 (1993).

The gene for GFP was first cloned by Prasher et al., *Gene,* 111:229–233 (1992), and cDNA for the protein produces a fluorescent product identical to that of native protein when expressed in prokaryotic (*E. coli*) and eucaryotic (*C. elegans*) cells; Chalfie et al., *Science,* 263:802–805 (1994). Importantly, exogenous substrates and cofactors are not required for GFP fluorescence in such cells; Id. As such, GFP is considered to have tremendous potential in methods to monitor gene expression, cell development, or as an in situ tag for fusion proteins; Heim et al., *P.N.A.S. USA,* 91:12501–12504 (1994).

Chalfie and Prasher, WO 95/07463 (March 16, 1995), describe various uses of GFP, including a method of examining gene expression and protein localization in living cells. Specifically, methods are described wherein: 1) a DNA molecule is introduced into a cell, said DNA molecule having DNA sequence of a particular gene linked to DNA sequence encoding GFP such that the regulatory element of the gene will control expression of GFP; 2) the cell is cultured in conditions permitting the expression of the fused protein; and 3) detection of expression of GFP in the cell, thereby indicating the expression of the gene in the cell. Methods such as those described by Chalfie and Prasher are advantageous compared to previously reported methods which utilized β-galactosidase fusion proteins; see e.g. Silhavy and Beckwith, *Microbiol. Rev.,* 49:398 (1985); Gould and Subramani, *Anal. Biochem.,* 175:5 (1988); Stewart and Williams, *J. Gen. Microbiol.,* 138:1289 (1992), or luciferases; Id., in that the need to fix cell preparations and/or add exogenous substrates and cofactors is eliminated.

Several groups have studied various GFP mutants in order to identify a GFP having improved fluorescent properties. For example, Heim et al., *P.N.A.S USA,* 91:12501–12504 (1994) report on GFP variants having significant alterations in the ratio of the two main wildtype excitation peaks. In particular, a $Ile^{167} \rightarrow Thr$ mutant had increased fluorescence at 475 nm excitation. Also identified was a mutant, $Tyr^{66} \rightarrow His$, which fluoresced blue.

Heim et al., *Nature,* 373:663–664 (1995) report that simple point mutations in Aequorea GFP bring its spectra closer to that of *Renilla reniformis* GFP, a protein with only one absorbance and excitation peak. In particular, a $Ser^{65} \rightarrow Thr$ mutant showed greatly increased brightness and rate of fluorophore generation as compared to wildtype Aequorea GFP.

Delagrave et al., *BIO/TECHNOLOGY,* 13:151–154 (1995) report on several Aequorea GFP variants that showed red-shifted excitation spectra similar to that of *Renilla reniformis* GFP, i.e., shift in excitation maxima from 393 nm to 498 nm. Delagrave et al. hypothesize that co-expression of GFP and red-shifted GFP (RSGFP) will enable the analysis of two proteins or promoters per cell or organism.

To date, there have been no reports of temperature sensitive GFP mutants having enhanced fluorescence at high temperatures, e.g., 37° C., where wildtype GFP does not fluoresce well. Such mutants would provide obvious and significant advantages for use as cell markers or protein expression indicators in prokaryotic and, especially, eucaryotic systems where the standard physiological temperature is 37° C.

SUMMARY OF THE INVENTION

Accordingly, it is the object of the present invention to provide novel mutants of the green fluorescent protein having improved fluorescent properties. The GFP mutants provided in accordance with the present invention exhibit improved solubility properties at higher temperatures and are able to fluoresce at 37° C. As such, these GFP mutants are particularly useful in fluorescence-activated cell sorting (FACS) screening methods for studying various vector components, e.g., promoters, repressors; for developing improved methods of monitoring and/or improving gene expression; and for studying the tissue specificity of a particular protein.

A preferred mutant of the present invention is a polypeptide having an amino acid sequence of a naturally occurring GFP molecule wherein at least one of the original amino acid residues is replaced by a substitution amino acid residue. In a particularly preferred embodiment, the phenylalanine at original amino acid position 64 is replaced by a leucine, and this $Phe^{64} \rightarrow Leu$ mutant has the ability to fluoresce at 37° C.

DETAILED DESCRIPTION OF THE INVENTION

The term "green fluorescent protein", as used herein, includes naturally occurring ("wildtype") green fluorescent protein, as well as non-naturally occurring polypeptides having an amino acid sequence sufficiently duplicative of that of naturally occurring green fluorescent protein which produce a fluorescent product identical to that of native protein when expressed in prokaryotic (*E. coli*) and eucaryotic (*C. elegans*) cells.

The term "mutant" as used herein refers to polypeptides wherein at least one of the naturally occurring ("original") amino acid residues is replaced by a substitution amino acid residue.

As employed herein the term "substitution amino acid" means an amino acid which replaces the naturally occurring amino acid, and which is different from the original amino acid.

As employed herein, "a vector component" of a gene is a DNA sequence necessary for the transcription/translation of the gene, e.g., promoters and repressors. Various classes of promoters and repressors are well known in the art and can be obtained commercially or assembled from the sequences and methods which are also well known in the art.

In one embodiment of the invention, the vector component is a version of the lactose inducible promoter. Lactose promoters are commonly known to suffer from "leakiness" problems in uninduced stationary phase cultures and such promoters are well known in the art; Studier et al., *J. Mol.*

Biol., 189:113–130 (1986). The "leakiness" problems associated with such promoters makes utilization of the promoters particularly problematic, especially in the commercial setting.

The GFP mutants of the present invention can be encoded, expressed, and purified by any one of a number of recombinant technology methods known to those skilled in the art. The preferred production method will vary depending upon many factors and considerations, including the cost and availability of materials and other economic considerations. The optimum production procedure for a given situation will be apparent to those skilled in the art through minimal experimentation.

DNA molecules containing DNA sequences encoding the GFP mutants of the present invention can be introduced into a variety of host cells, said host cell selected from the group consisting of bacterial cells, yeast cells, fungal cells, insect cells and plant or animal cells. Suitable animal cells include Hela cells, Cos cells and various mammalian cells, e.g. zebrafish, C. elegans. The methods by which the exogenous genetic material is introduced into such host cells are well known in the art.

DNA sequences coding for the GFP mutants of the present invention are provided and such sequences may include the incorporation of codons "preferred" for expression by selected E. coli host strains ("E. coli expression codons"), the provision of sites of cleavage by restriction endonuclease enzymes, and/or the provision of additional initial, terminal, or intermediate DNA sequences which facilitate construction of readily expressed vectors.

In one embodiment, the invention provides a bacteria cell capable of expressing the GFP mutants. In a preferred embodiment the bacterial cell is E. coli, wherein the GFP mutants can be expressed at particularly high levels, with the resulting expression product being subsequently purified to near homogeneity using procedures known in the art.

The GFP mutants of the present invention exhibit surprisingly increased solubility at higher temperatures. Unlike wildtype GFP, the GFP mutants of the present invention possess excellent fluorescent properties at 37° C. While it is known that GFP mutants having different fluorescent properties could be obtained through substitution of certain amino acids, substitution for the phenylalanine residue at position 64 of wildtype GFP alone was not known to be significant in increasing the solubility of GFP at higher temperatures. This is demonstrated by the ability of the Phe$^{64}$→Leu mutant to fluoresce at 37° C.

Other additions, substitutions, and/or deletions may be made to the GFP mutants of the present invention. For example, the GFP mutant may also optionally include a second amino acid substitution at position 65 or 66 of wildtype GFP. In addition, the GFP mutants of the present invention which are expressed from E. coli host cells may include an initial methionine amino acid residue. Alternatively, one or more of the terminal amino acid residues may be deleted from the DNA sequence, as is known to those skilled in the art, while substantially retaining the improved solubility properties of the GFP mutants.

Because of their improved solubility properties, the novel GFP mutants of the present invention are particularly well suited for use in fluorescence-activated cell sorting (FACS); Melamed et al., Flow Cytometry & Sorting, Second Edition, Wiley-Liss, N.Y. (1990) screening methods for studying various vector components, e.g., promoters, repressors; for developing improved methods of monitoring and/or improving gene expression; and for studying the tissue specificity of a particular protein/ligand.

In one aspect of the invention, a method is provided wherein the GFP mutants are used to identify cells having improved promoter "leakiness/expression" characteristics. Generally, the method comprises:

(1) identifying the particular promoter to be evaluated;
(2) construction of a plasmid containing the promoter and the GFP mutant cloned behind the promoter;
(3) introduction of the plasmid into a particular cell;
(4) mutagenesis of the cells with ethyl methane sulfonate (EMS) or other methods known to those skilled in the art; and (5) FACS sorting for cells having low levels of fluorescence, i.e., having improved "leakiness" characteristics.

In a another aspect of the invention, a method is provided which allows for easy and effective monitoring of the expression of a particular protein, under various conditions. This method utilizes protein-GFP mutant "fusions" wherein said protein is fused in frame with the GFP mutant at the C-terminus of the protein. Generally, the method comprises:
(1) introducing into a cell a DNA molecule having a DNA sequence encoding a GFP mutant linked to the DNA sequence of a particular gene at the C-terminus of the gene;
(2) mutagenesis of the cells with ethyl methane sulfonate (EMS)or other methods known to those skilled in the art; (3) culturing the cell under conditions which permit the expression of the mutagenized fused proteins; and (4) FACS sorting for cells with increased fluorescence, i.e., improved expression characteristics.

Also provided is a method for providing GFP mutant-protein "fusions" wherein said GFP mutant is fused in frame with the protein at the C-terminus of the GFP mutant. Importantly, these fusion proteins can be used to study the tissue distribution/specificity of the protein. Generally, the method comprises:
(1) introducing into a cell a DNA molecule having a DNA sequence encoding a GFP mutant linked to the DNA sequence of a particular gene encoding a particular protein at the C-terminus of the GFP mutant;
(2) expression and subsequent purification of the GFP-protein fusion; (3) use of the GFP-protein fusion to identify said protein receptors in a particular tissue specimen.

In one embodiment of the invention, the protein used to make the GFP:protein fusion is keratinocyte growth factor (KGF); Finch et al., Science, 245:752–755 (1989). KGF is a member of the fibroblast growth factor (FGF) family and binds to cell surface receptors on Balb/MK keratinocytes to which aFGF and bFGF may also bind. Bottaro, et al, J. Biol. Chem., 265, 12767–12770 (1990). KGF exhibits potent mitogenic activity for a variety of cells, and is distinct from the known FGFs in that it is not mitogenic for fibroblasts or endothelial cells. Rubin et al,, Proc. Natl. Acad. Sci. USA, 86:802–806 (1989).

The following examples are provided to aid in the understanding of the present invention, the true scope of which is set forth in the appended claims. It is understood that modifications can be made in the procedures set forth, without departing from the spirit of the invention.

EXAMPLE 1

In this example, the preparation of the wildtype GFP and novel GFP mutants of the present invention is described. The procedures used in this, and the other examples of the present invention, utilized various synthetic oligonucleotides, and polymerase chain reaction (PCR)

technology; R. K. Saiki et al., *Science*, 239:487 (1988). All oligonucleotides (and their respective Sequence Listing Nos.) used throughout Examples 1–6 are listed Table 1.

TABLE 1

Oligonucleotides Utilized To Prepare wildtype GFP/GFP Mutants/Fusion Proteins

| | |
|---|---|
| 909-57 (SEQ ID NO:1) | 909-58 (SEQ ID NO:2) |
| 909-59 (SEQ ID NO:3) | 909-60 (SEQ ID NO:4) |
| 909-61 (SEQ ID NO:5) | 909-62 (SEQ ID NO:6) |
| 909-63 (SEQ ID NO:7) | 909-64 (SEQ ID NO:8) |
| 909-65 (SEQ ID NO:9) | 909-66 (SEQ ID NO:10) |
| 909-67 (SEQ ID NO:11) | 909-68 (SEQ ID NO:12) |
| 938-70 (SEQ ID NO:13) | 909-71 (SEQ ID NO:14) |
| 909-72 (SEQ ID NO:15) | 909-73 (SEQ ID NO:16) |
| 909-74 (SEQ ID NO:17) | 909-75 (SEQ ID NO:18) |
| 909-76 (SEQ ID NO:19) | 909-77 (SEQ ID NO:20) |
| 909-78 (SEQ ID NO:21) | 909-79 (SEQ ID NO:22) |
| 909-80 (SEQ ID NO:23) | 909-81 (SEQ ID NO:24) |
| 909-82 (SEQ ID NO:25) | 909-56 (SEQ ID NO:26) |
| 909-69 (SEQ ID NO:27) | 884-24 (SEQ ID NO:28) |
| 738-30 (SEQ ID NO:29) | 315-22 (SEQ ID NO:30) |
| 938-71 (SEQ ID NO:31) | 938-70 (SEQ ID NO:32) |
| 938-69 (SEQ ID NO:33) | 938-68 (SEQ ID NO:34) |
| 938-67 (SEQ ID NO:35) | 938-66 (SEQ ID NO:36) |
| 938-65 (SEQ ID NO:37) | 1040-9 (SEQ ID NO:38) |
| 1040-7 (SEQ ID NO:39) | 943-12 (SEQ ID NO:40) |
| 749-8 (SEQ ID NO:41) | 996-8 (SEQ ID NO:42) |
| 769-31 (SEQ ID NO:43) | |

Preparation of wildtype GFP and GFP Phe$^{64}$→Leu Mutant

Part 1

The amino acid sequence M62653 (Genebank) was initially used as the basis for the wildtype GFP gene, and a strategy devised wherein various synthetic oligonucleotides (see Table 1) were ligated together using standard ligation conditions to form a mixture which was then used as a template in PCR to amplify the GFP gene in the following steps:

(1) oligonucleotides 909-57 through 909-68 and 909-70 through 909-82 (150 pmol each) were phosphorylated in 50 mM Tris-HCl pH 7.4, 5 mM MgCl$_2$, 5 mM DTT, 1 mM ATP and 10 units T4 polynucleotide kinase in a 20 µl reaction at 37° C. for 20 minutes. Reactions were terminated by heating to 70° C. for 30 minutes. Oligonucleotides 909-56 and 909-69 were then combined with the phosphorylated oligonucleotides above in 100 mM Tris-HCl pH 7.4, 10 mM MgCl$_2$, 10 mM DTT, 2 mM ATP, 5% polyethylene glycol (PEG) in 190 µl. The mixture was heated to 70° C. and slow cooled to room temperature (RT) Forty units of T4 DNA ligase was added and the mixture incubated overnight at 16° C.;

(2) because the ligation mixture from step (1) failed to produce a visible band of the correct size, oligonucleotides 909-56/909-73 and oligonucleotides 909-69/909-63 were used to amplify the ligation mixture. Standard conditions for the PCR reactions were: 1× Boehinger-Mannheim Taq PCR buffer, 1 unit Taq DNA polymerase, 200 µM of each dNTP, 1 pmol/µl of each primer and 4 µl of ligation mix as template. The above reactions were done in 100 µl. The PCR program was: 94° C., 30 sec; 50° C., 30 sec; 72° C., 30 sec and this was repeated for 30 cycles. All PCR reactions were performed on a Perkin Elmer Cetus GeneAmp PCR System 9600 and all reactions were cooled to 4° C. following the final cycle;

(3) 20 µl of each PCR reaction were purified using the Geneclean Kit (Bio 101). The 909-56/909-73 reaction was digested with XbaI/AccI and the 909-69/909-63 reaction was digested with AccI/HindIII by standard methods. The digests were electrophoresed on an agarose gel and the digested fragments were cut out of the gel, purified using Geneclean, and set for ligation in 50 mM Tris-HCl pH 7.4, 5 mM MgCl$_2$, 5 mM DTT, 5% PEG, 1 mM ATP and 10 units of T4 DNA ligase (standard ligation conditions). The ligation was carried out at 16° C. overnight;

(4) the ligation mix from (2) was used as a template for a PCR reaction of the full length wildtype GFP gene. Oligos 909-56/909-69 and 884-24/909-69 were run in a standard PCR mix using 2.5 µl of ligation mix as template and a 100 µl reaction volume. The cycles for the PCR were: 94° C., 1 min; 37° C., 1 min; 72° C., 3 min and was repeated 25 times (Program 1). 50 µl of each of the 2 reactions above were purified by Geneclean, combined, and then set for XbaI/HindIII digestion overnight. The digestion products were electrophoresed on an agarose gel and the products were cut out and purified by Geneclean. The purified fragment was ligated by the standard method with a XbaI/HindIII digested pCFM-1656 vector (ATCC® No. 69576). The ligation mix (3.5 µl) was electroporated into 40 µl competent FM5 cells (ATCC® No. 53911) using a Bio-Rad Gene Pulser electroporation device. The electroporation cuvettes had a 0.2 cm spacing and the charge delivered was 2.25 volts (standard electroporation conditions);

(5) the resulting colonies were screened for insert by PCR using oligos 738-30/315-22 in a standard 20 µl PCR reaction using Program 1. The transformed cells served as templates. Several clones were identified as having the correct sized insert as judged by an agarose gel. They also had the expected restriction patterns. However, none of them glowed when induced. Furthermore, when sequenced, each clone identified contained multiple mutations as compared to the designed sequence. One clone, designated pCFM1656-GFP1.2ab, was then prepared and found to have only one basepair mutation as compared to the designed sequence. This pCFM1656-GFPI.2ab clone still did not glow however.

Part 2

Another GFP sequence, M62654 (Genebank) was next used as a basis for the wildtype GFP and a new strategy devised wherein the pCFM1656-GFP1.2ab clone described above was used as a template in a series of overlap PCR reactions as described as follows:

(1) oligonucleotide pairs 909-56/938-71, 938-70/938-69, 938-68/938-67, and 938-66/938-65 were used in 4 separate 100 µl PCR reactions under standard conditions. The PCR cycles were 94° C., 1 min; 45° C., 1 min; 72° C., 2 min and this was repeated 25 times. The products from these reactions were run on an agarose gel and purified using Geneclean. The first 2 reactions were then combined and used as a template for a second round of PCR using 909-56/938-69. Similarly, the last 2 reactions were combined and served as a template with the 938-68/938-65 oligos. The products of the secondary rounds were run on an agarose gel and purified by Geneclean. A combination of the 2 products served as a template for a third round of PCR using oligos 909-56/938-65. This product was Geneclean purified, digested with XbaI/EcoRI, ligated with similarly digested pCFM-1656 and electroporated into FM5. A small percentage of the colonies from this transformation did glow when induced;

(2) this clone was then sequenced, and found to have 2 mutations from the desired sequence: one gave a valine to isoleucine change at amino acid 29; the other was a phenylalanine to leucine change at amino acid 64 (designated $Val^{29} \rightarrow Ile; Phe^{64} \rightarrow Leu$ mutant);

(3) the $Val^{29} \rightarrow Ile; Phe^{64} \rightarrow Leu$ mutant was then subcloned to another expression plasmid designated pAMG11. The pAMG11 plasmid utilizes an inducible lactose promoter to regulate expression and is derived from the plasmid pCFM1656 by making a series of site-directed base changes by PCR overlapping oligonucleotide mutagenesis (the base pair changes start with the BglII site (plasmid base pair #180) immediately 5' to the plasmid replication promoter $P_{cop}B$ and proceed toward the plasmid replication genes. The specific base pair changes are listed in Table 2 below). The pAMG11 vectors were then electroporated into GM120 host cells (deposited with ATCC® on May 1, 1996, No. 55764) and the clone designated pAMG11-$Val^{29} \rightarrow Ile; Phe^{64} \rightarrow Leu$ obtained.

TABLE 2

Base pair changes used for derivation of pAMG11 from pCFM1656

| pAMG11 bp # | bp in pCFM1656 | bp change for pAMG11 |
|---|---|---|
| # 204 | T/A | C/G |
| # 428 | A/T | G/C |
| # 509 | G/C | A/T |
| # 617 | — | insert two G/C |
| # 679 | G/C | T/A |
| # 980 | T/A | C/G |
| # 994 | G/C | A/T |
| # 1004 | A/T | C/G |
| # 1007 | C/G | T/A |
| # 1028 | A/T | T/A |
| # 1047 | C/G | T/A |
| # 1178 | G/C | T/A |
| # 1466 | G/C | T/A |
| # 2028 | G/C | bp deletion |
| # 2187 | C/G | T/A |
| # 2480 | A/T | T/A |
| # 2499-2502 | AGTG<br>TCAC | GTCA<br>CAGT |
| # 2642 | TCCGAGC<br>AGGCTCG | bp deletion |
| # 3435 | G/C | A/T |
| # 3446 | G/C | A/T |
| # 3643 | A/T | T/A |
| # 4489-4512 | — | insert<br>GAGCTCACTAGTGTCGACCTGCAG<br>CTCGAGTGATCACAGCTGGACGTC |

4358-4438 Substitute pCFM1656 DNA sequence with
          the following:
5'-      CTCATAATTTTTAAAAAATTCATTTGACAAATGCTAAAATT-
3'- TGCAGAGTATTAAAAATTTTTTAAGTAAACTGTTTACGATTTTAA-
    -CTTGATTAATATTCTCAATTGTGAGCGCTCACAATTTAT      3'
    -GAACTAATTATAAGAGTTAACACTCGCGAGTGTTAAATAGC 5'

(4) another GFP clone identified from Part 2 step (1) above (designated pCFM1656-GFP#2) was wild type at amino acid 64. Therefore, the NcoI/PstI fragment from pCFM1656-GFP#2 was used to replace the same region in the pAMG11-$Val^{29} \rightarrow Ile; Phe^{64} \rightarrow Leu$ clone, the vector electroporated into GM120 cells, and the pAMG11-$Val^{29} \rightarrow Ile$ clone obtained. This clone glowed very weakly at low temperature when uninduced. This suggested that the $Val^{29} \rightarrow Ile$ mutation was a relatively conservative substitution, and that the $Phe^{64} \rightarrow Leu$ mutation was an improvement over the wild type gene.

Part 3

The pAMG11-$Val^{29} \rightarrow Ile$ clone was then used as a template for two primary PCR reactions using the oligo pairs 738-30/938-71 and 938-70/315-22 in a 50 μl reaction under standard conditions except that 1 unit of Pwo polymerase was used instead of Taq polymerase. The PCR cycles were 94° C., 1 min; 45° C., 1 min; 72° C., 2 min and this was repeated 25 times. The products from the reactions were run on an agarose gel and purified using Geneclean. The first 2 reactions were then combined and this was used as a template for a second round of PCR using the primer pair 738-30/315-22 under the same conditions as above. The product was Genecleaned, digested with XbaI/HindIII, electrophoresed on an agarose gel, excised and purified using Geneclean and ligated with pAMG11 vector that had been also digested with XbaI/HindIII under standard ligation conditions. Electroporation of the ligation mix into strain XLI-Blue yielded a clone that was as originally designed based on the M62654 sequence. This clone was designated pAMG11-wildtype GFP. This clone gives a wild type protein that behaves like the pAMG11-$Val^{29} \rightarrow Ile$ mutant, i.e. it is a temperature sensitive GFP.

Part 4

The XbaI/NcoI fragment from the pAMG11-wildtype GFP clone was swapped with the same fragment from the pAMG11-$Val^{29} \rightarrow Ile; Phe^{64} \rightarrow Leu$ clone using standard cloning procedures to create the pAMG11-$Phe^{64} \rightarrow Leu$ clone. When used to transform GM120 cells, we found that the pAMG11-$Phe^{64} \rightarrow Leu$ clone had the same properties as the pAMG11-$Val^{29} \rightarrow Ile; Phe^{64} \rightarrow Leu$ clone, i.e., improved fluorescence at 37° C. The DNA and amino acid sequence of the pAMG11-$Phe^{64} \rightarrow Leu$ clone is depicted in SEQ ID NO:44.

EXAMPLE 2

In this example, experiments were performed in order to determine why the pAMG11-$Phe^{64} \rightarrow Leu$ and pAMG11-$Val^{29} \rightarrow Ile; Phe^{64} \rightarrow Leu$ mutants performed better than the pAMG11-wildtype GFP.

The pAMG11-$Phe^{64} \rightarrow Leu$ and pAMG11-wildtype GFP plasmids described in Example 1 were expressed at 37° C. and total cell protein run on an acrylamide gel, stained and analyzed for the level of expression from the two plasmids. The two plasmids expressed similar amounts of protein so the mutation did not lead to a change in expression level.

Cells were then examined under the microscope. The wildtype strain had large inclusion bodies (these are made up of insoluble, incorrectly folded protein) whereas the $Phe^{64} \rightarrow Leu$ mutant had much smaller (and fewer) inclusion bodies. This suggested that the mutant lead to an increase in the percentage of soluble protein at elevated temperatures. Examination of the cells under a fluorescent microscope showed that the protein found in inclusion bodies did not glow whereas that found in the soluble cytoplasmic section does. Thus, the mutants perform better at high temperature because the $Phe^{64} \rightarrow Leu$ mutation increases the solubility of the protein at elevated temperatures.

EXAMPLE 3

In this example, the preparation of the novel GFP double mutants of the present invention is described.
Preparation of the $Phe^{64} \rightarrow Leu-Ser^{65} \rightarrow Thr$ Mutant The $Ser^{65} \rightarrow Thr$ GFP mutant has been reported to produce a shift in the excitation spectra; Nature 373:663–664 (1995). We created a $Phe^{64} \rightarrow Leu; Ser^{65} \rightarrow Thr$ double mutant by using oligo pair 1077-13/943-12 (see Table 1) on the pAMG11-$Phe^{64} \rightarrow Leu$ template in a standard 20 μl reaction with 25 PCR cycles of 94° C., 10 sec; 45° C. 30 sec; 72° C., 3 min. A portion of the reactions were purified using Qiagen's QIAquick Spin PCR purification Kit as per the manufacturer's instructions. The purified PCR product was digested with PmlI/NcoI. The digested product was run on an agarose gel and purified using the OIAquick Kit. This was ligated into a similarly cut and purified pAMG11-wildtype GFP vector. When tested, this double mutant was found to be more soluble at 37° C. and had the shifted excitation spectra.

Preparation of the $Phe^{64} \rightarrow Leu;Tyr^{66} \rightarrow His$ Mutant

In another example we combined the $Phe^{64} \rightarrow Leu$ mutation with a mutation that produces a shift in the emission spectra from green to blue, $Tyr^{66} \rightarrow His$ (PNAS 91:12501–504 (1994)). We created this double mutant by using overlap PCR. The primary oligo pairs were 1040-9/938-70 (see Table 1) with the pAMG11-$Phe^{64} \rightarrow Leu$ template and 1040-7/943-12 (see Table 1) with the pAMG11-wildtype GFP template in a standard 50 µl reaction with 25 PCR cycles of 94° C., 10 sec; 45° C. 30 sec; 72° C., 3 min. A portion of the reactions were run on an agarose gel and purified using the OIAquick Kit. A portion of the purified PCR products were combined and used in a secondary PCR reaction with the 938-70/943-12 oligo pair. A portion of that reaction was purified using Qiagen's QIAquick Spin PCR purification Kit. The purified PCR product was then digested with PmlI/NcoI. The digested product was run on an agarose gel, purified using the OIAquick Kit, and ligated into a similarly cut and purified pAMG11-$Val^{29} \rightarrow Ile;Phe^{64} \rightarrow Leu$ vector. When tested, this double mutant was both blue and thermally tolerant.

In summary, we have found that the property of increased solubility at elevated temperatures can be combined with other mutations to yield a double mutant with the combined phenotype of the two independent mutations. As such, the property of improved solubility at higher temperatures conferred by the pAMG11-$Phe^{64} \rightarrow Leu$ mutation can be added to other mutations, resulting in GFP double mutants that have clear advantages over the single mutants.

EXAMPLE 4

In this example, the pAMG11-$Phe^{64} \rightarrow Leu$ mutant was used in a method for identifying cells with improved promoter leakiness/expression characteristics.

A GM120 host strain containing pAMG11-$Phe^{64} \rightarrow Leu$ was mutagenized with ethyl methane sulfonate (EMS) by a published protocol (A Short Course in Bacterial Genetics, Laboratory Manual, Cold Spring Harbor Press, 1992, pg. 135–142). Uninduced cells (overnight recovered) were FACS sorted for cells that leaked less when in the uninduced stationary phase.

A large number of candidates were sorted which had reduced leakage from the promoter in the uninduced state as judged by the FACS, i.e, they had less fluorescence. These candidates were plated to LB plates at 37° C. and grown overnight. Leakiness was assessed by shining a long wave UV monitor over the plated cells and looking for those that glowed more weakly than the control strain.

The candidates glowing more weakly than the control were then purified and further tested for leakiness and expression by running total cell protein from uninduced and induced 28° C. cultures on acrylamide gels vs. the starting strain. The gels were stained with Coomassie and were visually assessed for improved promoter characteristics vs. the starting strain. The results indicate that there are strains possessing improved promoter leakiness characteristics.

EXAMPLE 5

In this example, the pAMG11-$Phe^{64} \rightarrow Leu$ mutant is used to develop an improved method for monitoring gene expression and identifying strains having increased gene expression.

A KGF-GFP fusion that fused a version of KGF in frame with pAMG11-$Phe^{64} \rightarrow Leu$ mutant at the C-terminus of KGF was created. The fusion was constructed using the following PCR-based method: the KGF DNA section was derived from cloned DNA (originally obtained by chemically synthesizing the DNA with E. coli optimized codons) (SEQ ID NO:45) using oligo pair 749-8/996-8 (see Table 1) The GFP section was derived from pAMG11-$Val^{29} \rightarrow Ile;Phe^{64} \rightarrow Leu$ DNA (SEQ ID NO:46) using oligos 769-31/315-22. The PCR was carried out in 100 µl reactions of 30 PCR cycles at 94° C., 20 sec; 37° C., 30 sec; 72° C., 30 sec. The products were run on an agarose gel and purified using the Qiaex II Kit as per the manufacturer's protocol.

Fusion of the KGF and GFP sections was achieved by: (1) PCRing the two products without any primers for 8 rounds at 94° C., 45 sec; 45° C., 45 sec; 72° C., 45 sec, creating the 5' fusion strand; (2) PCRing the two products with oligo 315-22 for 12 rounds at 94° C., 45 sec; 45° C., 45 sec; 72° C., 45 sec, creating the homologous 3' strand; (3) amplification of the sequence by adding end oligos 749-8 and 315-22 and amplifying an additional 30 rounds. The resulting fragment was run on a gel, purified by the QiaexII method and digested with XbaI/BamHI. The product was then ligated into pAMG11 that had been similarly digested and purified.

A GM120 host strain containing this fusion was mutagenized with EMS (ethyl methane sulfonate) for 45 minutes by a published protocol (A Short Course in Bacterial Genetics, Laboratory Manual, Cold Spring Harbor Press, 1992, pg. 135–142). The cells were recovered in LB at 28° C. overnight, subcultured to LB+Kan and induced for expression with IPTG for 6 hours. Cells were spun down and resuspended with PBS to be FACS sorted for increased glowers. The sorted cells were screened by plating them onto LB plates and transferring the resultant colonies to inducing plates of LB+Kan+IPTG using sterilized circular Whatman filters. Colonies were induced for at least 8 hours. Enhanced glowers were then picked and screened for increased production of KGF. We were able to find several strains with improved KGF expression using this method.

EXAMPLE 6

In this example, the improved solubility of the GFP mutant was exploited to prepare a unique GFP-KGF fusion protein. The feasibility of using the GFP-KGF fusion to localize KGF receptors occurring in non glandular rat stomach was then evaluated. Preparation of the GFP-KGF Fusion
Part 1

The GFP-KGF fusion was prepared as follows: the pAMG11-$Phe^{64} \rightarrow Leu$ gene was modified at its C-terminus to include three additional functional components; namely, a hexahistidine tag (amino acids 239–244) for rapid purification, a c-myc antibody recognition epitope (amino acids 245–254), and a kallikrein cleavage site preceded by polyasparagine spacer (amino acids 255–272). Overlapping synthetic oligonucleotides were assembled to create a duplex DNA which, after digestion with SacI and BamHI restriction endonucleases, was used to replace the 3'-terminal SacI to BamHI region of the original pAMG11-$Phe^{64} \rightarrow Leu$ gene. The new construct had the sequence depicted in SEQ ID NO:47.
Part 2

The version of keratinocyte growth factor (KGF) used in this example was one lacking the first 23 amino acids of mature KGF. The gene was synthesized by PCR with the forward primer being designed to create a SexAI restriction site followed by the last seven codons of the modified GFP Phe[64]→Leu from Part 1 fused to the first codon of KGF. The product of the PCR reaction was digested with SexAI and BamHI and ligated into modified pAMG11-Phe[64]→Leu similarly digested. Ligated DNA was transformed into FM15 (deposited with ATCC® on May 1, 1996, No. 55765) host cells. Clones were screened for the ability to express GFP-KGF when induced with IPTG. One of the clones was selected for further work. Its plasmid was isolated and the sequence of the recombinant gene was determined. The sequence of the 412 amino acid GFP-KGF fusion is depicted in SEQ ID NO:48.

Purification of the GFP-KGF Fusion

The GFP-KGF fusion was prepared and purified as described by Suzuki et al., *FEBS Letters,* 328:17–20 (1993). However, because the isoelectirc point of GFP-KGF was determined to be 2.55 pH units lower than that of KGF, the S-Sepharose column was equilibrated and run at pH 6.2 instead of pH 7.5.

Use of the GFP-KGF Fusion to Localize KGF Receptors

The GFP-KGF fusion prepared above was then tested for it's ability to localize KGF receptors as follows:

A normal rat stomach was collected at necropsy, opened along the greater curvature, and rinsed in PBS to remove gastric contents. The stomach was then sectioned so that narrow strips of tissue were prepared which could be oriented in a CryoMold filled with OCT embedding compound so that cross sections of the stomach wall could be cut. The mold was snap frozen in isopentane cooled liquid nitrogen. The frozen block was stored at −80° C. until use. Cryostat sections were cut (5 $\mu$m) and held frozen in the cryostat until staining. Staining was performed on the same day as sectioning.

A GFP-KGF fusion prepared as described above, in PBS, at a concentration of 0.5 mg/ml, was used in the staining protocol. A dilution series of 1:10, 1:20, 1:40, and 1:80 was done giving working concentrations of $5\times10^{-5}$, $2.5\times10^{-5}$, $1.25\times10^{-5}$, and $6.25\times10^{-6}$, respectively. Dilutions and washes were done with Dulbecco's PBS containing calcium and magnesium. The staining protocol is conducted as follows: (1) frozen sections were air dried; (2) slides are rinsed in PBS; (3) tissue sections are covered with a GFP-KGF fusion dilution or with PBS and binding allowed to take place at room temperature for 45 minutes; (4) all slides are thoroughly washed with PBS for 3×5 minutes; (5) slides are fixed in 3% formalin, 60% acetone, 37% PBS for 1 minute at room temperature; (6) slides are washed with PBS for 2×5 minutes, followed by multiple changes of deionized water; (7) coverslip in aqueous mountant (Shandon Immu-Mount).

Sections were then examined on a Nikon FXA microscope (Nikon) fitted with a fluorescence lamp and using a FITC cube. When examined, the slide treated with PBS only showed no signal on any portion of the tissue. The slide treated with 1:40 and 1:80 GFP-KGF fusion dilutions showed very weak signal. However, the slide treated with 1:10 and 1:20 GFP-KGF fusion dilutions showed strong signal in the non glandular stomach that seemed to be at the epithelial muscularis junction. The glandular stomach showed scattered areas of stain somewhat consistent with the in situ pattern normally seen; Finch et al., *Developmental Dynamics,* 203:223–240 (1995). In a separate experiment performed by the above procedure using a slide containing unlabeled KGF (i.e., KGF without GFP), no signal was detected.

The data demonstrate that the GFP-KGF fusion can effectively and efficiently be used to localize KGF receptors in different tissues.

What is claimed is:

1. A mutant of the green fluorescent protein (GFP) having the amino acid sequence set forth in SEQ ID NO:49 which is modified by one or more of the following substitutions:

Val$^{29}$→Ile, Tyr$^{66}$→His; Ile$^{167}$→Thr, wherein said mutant has improved solubility properties at 37° C. as compared to naturally occurring GFP.

2. A mutant green fluorescent protein (GFP) of claim 1 having the amino acid sequence set forth in SEQ ID NO:49 which is modified by one or more of the following substitutions in amino acid sequence:

Val$^{29}$→Ile,

Tyr$^{66}$→His,

Ile$^{167}$→Thr.

3. A nucleic acid comprising a sequence encoding the mutant GFP of claim 1.

4. A nucleic acid of claim 3, wherein the encoding sequence is operatively linked to an expression control sequence.

5. A host cell stably transformed or transfected with the nucleic acid according to claim 3 or 4.

6. A host cell according to claim 5, which expresses said mutant GFP encoded by said nucleic acid.

* * * * *

UNITED STATES PATENT AND TRADEMARK OFFICE
CERTIFICATE OF CORRECTION

PATENT NO.    : 6,096,865
DATED         : August 1, 2000
INVENTOR(S)   : Mark Michaels It is certified that error appears in the above-identified patent and that said Letters Patent is hereby corrected as shown below:

<u>Column 7,</u>
Table 2, Line 49, should read --
3'- TGCAGAGTATTAAAAATTTTTTAAGTAAACTGTTTACGATTTTAAGAA- --
Table 2, Line 50, should read --
-GATTAATATTCTCAATTGTGAGCGCTCACAATTTAT 3' --
Table 2, Line 51, should read --
-CTAATTATAAGAGTTAACACTCGCGAGTGTTAAATAGC 5' --

Signed and Sealed this

Twenty-fourth Day of December, 2002

JAMES E. ROGAN
*Director of the United States Patent and Trademark Office*